United States Patent
Wulfsberg

(10) Patent No.: US 6,537,210 B1
(45) Date of Patent: Mar. 25, 2003

(54) ENDOSCOPE WITH A MOVABLE COMPONENT

(75) Inventor: Jens Peter Wulfsberg, Neritz (DE)

(73) Assignee: Olympus Winter & IBE GmbH, Hamburg (DE)

(*) Notice: Subject to any disclaimer, the term of this patent is extended or adjusted under 35 U.S.C. 154(b) by 0 days.

(21) Appl. No.: 09/980,397
(22) PCT Filed: May 22, 2000
(86) PCT No.: PCT/EP00/04634
§ 371 (c)(1), (2), (4) Date: Nov. 29, 2001
(87) PCT Pub. No.: WO00/78205
PCT Pub. Date: Dec. 28, 2000

(30) Foreign Application Priority Data

Jun. 18, 1999 (DE) .......................... 199 27 816

(51) Int. Cl.⁷ ................................. A61B 1/00
(52) U.S. Cl. .................. 600/173; 600/167; 600/163
(58) Field of Search ................. 600/106, 112, 600/118, 129, 163, 167, 168, 173, 174; 403/DIG. 1; 359/822, 823, 824

(56) References Cited

U.S. PATENT DOCUMENTS

| | | | |
|---|---|---|---|
| 5,056,902 A | * 10/1991 | Chinnock et al. | 359/503 |
| 5,575,754 A | * 11/1996 | Konomura | 600/117 |
| 5,593,437 A | * 1/1997 | Arita et al. | 623/6.22 |
| 5,706,143 A | * 1/1998 | Hipp | 359/624 |
| 5,836,867 A | 11/1998 | Speier et al. | |
| 5,978,161 A | * 11/1999 | Lemke | 359/824 |
| 5,995,293 A | * 11/1999 | Derkits et al. | 359/642 |

FOREIGN PATENT DOCUMENTS

| | | |
|---|---|---|
| DE | 195 21 654 A1 | 12/1996 |
| DE | 196 18 355 A1 | 11/1997 |
| DE | 197 13 276 A1 | 10/1998 |
| DE | 88 10 044 U | 11/1998 |

* cited by examiner

Primary Examiner—John P. Ledbecker
(74) Attorney, Agent, or Firm—Rankin, Hill, Porter & Clark LLP

(57) ABSTRACT

The invention relates to an endoscope with a hermetic housing wall (1) and containing an optic element (5, 11) which is adjusted by a drive element (6, 17) powered in turn by a magnet (7, 18) configured outside the wall (1). The optic elements (5, 11) can be held in specific adjustment positions by a detent device (9, 10, 19) in such manner that the force of the magnet (7, 18) shall move it from one adjustment position into another. The magnet (7, 18) is mechanically separate from the endoscope.

3 Claims, 1 Drawing Sheet

ENDOSCOPE WITH A MOVABLE COMPONENT

BACKGROUND OF THE INVENTION

1. Field of the Invention

The present invention relates to an endoscope with a sealed housing wall and an element configured therein, the element being adjustable by a drive element affixed thereto.

2. Description of Related Art

Endoscopes of the aforementioned type are fitted with means which, within a sealed housing wall, must be protected against environmental factors. Such means, in particular, are imaging devices such as lens optics or an electronic camera, light transmitting elements such as fiber optics or other sensitive optical or an electronic devices. Such devices are protected in the space enclosed by the sealed housing wall from ambient humidity and vapors.

Endoscopes of this kind already are used medically, the housing protecting against body fluids, cleaning and sterilization.

Component displacement is implemented using magnetism applied across the nonmagnetic housing and, therefore, does not require applied sliding motions or other elements that might jeopardize the sealing of the housing. As a result, the housing is well sealed and, in particular, such housing also allows very frequent steam autoclaving for complete sterilization.

The displaceable component may be used to drive electrical switches within the endoscope, to switch valves, for instance, for aspiration or rinsing lines and, in particular, to adjust optics for instance to focus them.

Endoscopes of this kind are known from the German patent documents A1 197 13 276 and A1 195 21 654. In these designs the drive means also is in the form of a permanent magnet. In the case of the design of the first document, several pairs of inner and outer magnets are used for the purpose of attaining an exact angular coupling. The ring magnetically rotated on the inside engages a displacement thread and, in this manner, is secured by friction. In the design known from the latter document, an inner magnet slides within a curved path which, again, is intended to secure it by friction. The purpose is to prevent the component from shifting when impacts should disengage the inner and outer magnets. However, such designs do not allow precise setting of the components because the inner magnet may stop at any position.

The known designs require mounting the magnet permanently on the endoscope. The adjustment component which, for that purpose, is present at the endoscope and which contains the magnet however also entails interstices and gaps between the adjustment component and the endoscope, and these interstices and gaps are difficult to access, to clean and to sterilize.

Because the adjustment component must always remain at the endoscope, even when not needed for adjustment, it may interfere with handling the endoscope and will add to its weight.

Furthermore, such an adjustment component may only be mounted on the main body and only may drive components within the main body. In the region of the endoscope's stem, that is in particular at the optical objective present at the stem's distal end zone, the state of the art will not allow adjustments because external adjusting means permanently affixed to the stem are precluded.

SUMMARY OF THE INVENTION

It is an object of the present invention to create an endoscope of the above discussed species that is free of external adjusting devices.

In the invention, the component is mechanically secured in given adjustment positions predetermined by design and it may be magnetically displaced using the force of a magnet overcoming the retention force of the securing element. The externally acting magnet is mechanically separate from the endoscope and need be brought into magnetical interaction only when adjustments are required. The externally acting magnet may be removed thereafter without endangering the new adjustment position of the component, which is held by the securing element. The endoscope, therefore, may be put to use without being hampered by an external adjusting means. This design moreover allows situating the component to be adjusted in the endoscope's stem zone, especially in the optical objective zone, which was heretofore unknown.

Illustratively, the securing element may be a friction brake securing the drive component's position and supplemented by a limit stop allowing precise position adjustment. Magnetic securing elements also are possible to constrain specified positions. Preferably, however, spring-loaded detent elements represent simple implementations to secure the component into specified positions.

The present invention also allows handling and/or adjustment of the optic objective at the distal stem zone. Required objective adjustments may be carried out there, for instance, focusing by axially displacing elements of the objective. Preferably, however, the present invention will also permit the endoscope's viewing direction to be adjusted. This feature is the answer to the surgeons' long-held hope, namely to change in simple manner the viewing direction, for instance from straight ahead to obliquely. This change does not entail a change of endoscope, merely with a brief stop in the surgical procedure, movement of a magnet permits an adjustment in the vicinity of the distal endoscope tip is made.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
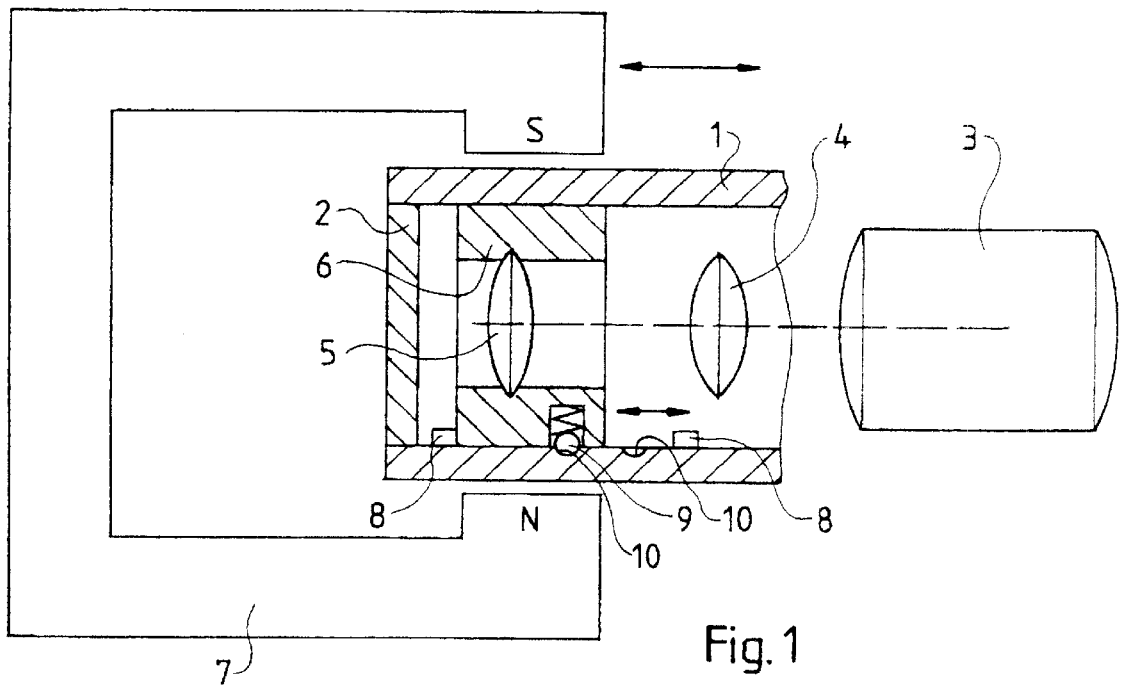
FIG. 1 is an axial section of the distal end zone of an endoscope and an externally mounted focusing magnet.

FIG. 1 shows a distal end zone of a stem of a medical endoscope fitted with a tube 1 constituting the stem and being sealed at its distal end by a window 2. A system of rod lenses acting as the image guide is mounted inside the tube 1 in the shown embodiment, of which one rod lens element 3 is shown explicitly. An objective, in this instance consisting of two lens elements 4 and 5, is present. The rod lens 3 and the objective lens element 4 are affixed in the tube 1 by omitted means.

The distal objective lens element 5 is supported in axially displaceable manner in the tube 1. The distal objective lens element 5 is mounted in a slide ring 6 which, as indicated, is guided in an axially displaceable manner inside the tube 1.

The tube 1 is made of a magnetically transparent, i.e. a non-magnetic, material such as an appropriately-alloyed high grade steel, which is also suitable for endoscope stems. The slide ring 6 is designed as a drive element actuated by a magnetic field and, illustratively, is a magnetically highly permeable material such as, for instance, material used for transformer sheet iron, which is subjected to high forces by magnetic fields.

A magnetic adjusting element is provided in the form of a magnet 7, which is physically separate from the endoscope and, in this embodiment, assumes the shape of a permanent magnet with poles N and S linked by a U-shaped yoke. A magnetic field between the poles N and S crosses an air gap which, for the case of the shown magnet 7, is as wide as the outside diameter of the tube 1.

Once the magnet 7 has been moved into the shown configuration to the distal end zone of the tube 1 inside the air gap, the magnetic field generated by the magnet will cross the slide ring 6 to which it applies strong forces. If the magnet 7 is displaced in the axial direction of the tube 1, the slide ring 6 follows on account magnetic forces. The distal objective lens element 5, therefore, is displaceable relative to the stationary objective lens element 4. Accordingly, depending on the objective's design and on whether either or both objective lens element(s) are designed to be displaceable in the shown manner, focusing or the like can then be carried out.

Upon the desired displacement of the displaceable objective lens element 5, the magnet 7 may be moved again. Thereupon, the slide ring 6 shall no longer be magnetically affected and, thus, is force-free. The slide ring, therefore, will remain in its newly adjusted position.

If the slide ring 6 were freely displaceable, that is if it were unsecured inside the tube 1, it might shift thereafter on its own. Such could happen, for instance, in the event of intense endoscope motion or by impacting the endoscope against a bench edge, on account of accelerational forces. Moreover, upon a motion of the magnet 7, the position of the slide ring 6 inside the opaque tube 1 cannot be seen from outside the tube 1. The slide ring 6 is always dragged along in a fuzzy way by the magnetic field and its position might never be precisely known.

For that reason two limit stops 8 are affixed inside the tube 1 to set the slide ring into its final position after its axial displacement. If the magnet 7 is just moved far enough in either direction, the ring 6 shall reliably have been displaced until resting against the limit stop 8.

When at the limit stops 8, the slide ring still must be secured against shifting due to accelerational forces. This goal may be attained, for instance, using a friction brake. The slide ring 6 may rest with adequate friction inside the tube 1 such that it may still be displaced by the magnetic field of the magnet 7 while being frictionally held in place if accelerated.

In this embodiment a spring-loaded detent device is used to secure the two limit positions of the slide ring 6 between which it can be switched. This spring-loaded detent device comprises a ball 9, which is outwardly loaded in an axial channel in the slide ring 6 by an illustrated spring, and, furthermore, two detent recesses 10 in the inner surface of the tube 1, which will receive the spring-loaded ball 9 when in the axial limit positions of the slide ring 6. The detent force on the ball 9 can be precisely set by means of the spring and, as a result, it shall be reliably held in place up to given accelerations. Nevertheless, the slide ring 6 may be moved, by the magnetic field of the magnet 7 overcoming the aforementioned detent force, from one into the other axial position. In this design the limit stops 8 may be eliminated from the design of the invention.

The design shown in FIG. 1 makes it possible to accurately switch the objective 4, 5 between two adjustment positions.

Figure 2:
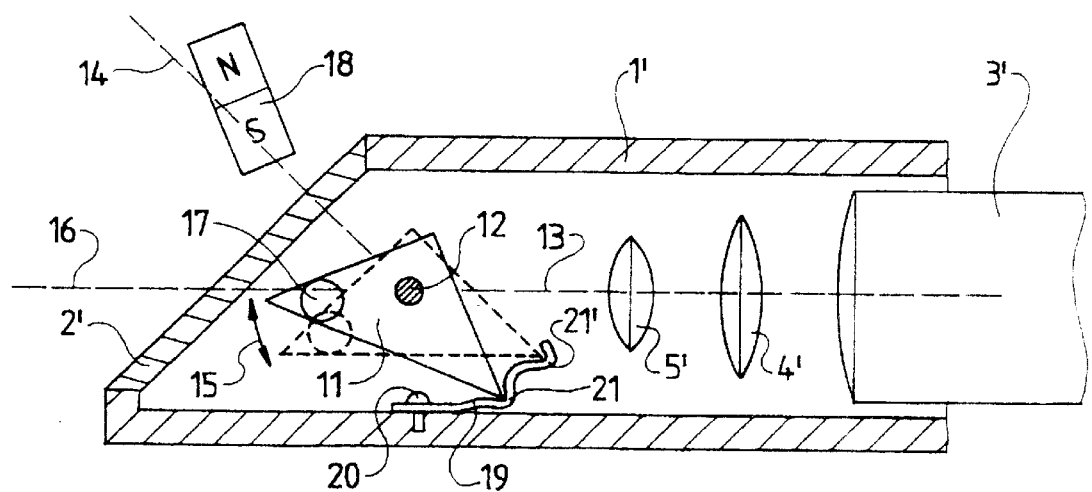
FIG. 2 is a section in the manner of FIG. 1 of an endoscope fitted with a magnet used to change the viewing direction.

FIG. 2 is a second embodiment of the invention and shows the distal end zone of an endoscope stem fitted with a tube 1' constituting, per se, the stem and firmly housing a rod lens 3' and two objective lens elements 4', 5' by housing means (not shown). A deflecting prism 11 acting as the displaceable component is mounted in front of the objective 4', 5' and is rotatably supported on the tube 1' by means of a shaft 12, which runs perpendicularly to the plane of the drawing. The distal aperture of the tube 1' is sealed obliquely by a window 2'. When the prism 11 assumes the rotational position indicated in solid lines, the prism will deflect the system optic axis 13 into an oblique viewing direction through the window 2' toward the dashed line 14. If, on the other hand, and as indicated in dashed lines, the prism has been rotated counter-clockwise through an angle denoted by the arrow 15, it will direct the optic axis 13 into the new and straight-ahead viewing direction 16. Accordingly, the endoscope viewing direction can be changed from oblique to straight ahead by rotating the prism 11 through an angle. In this instance the prism is a Dove prism. However, another system changing the viewing direction by angular adjustment also may be used. For instance, it is also contemplated to use rotating or swing mirrors that are, respectively, rotated or pivoted in relation to the desired change in viewing direction.

A drive element 17 is affixed to the prism 11 outside the shaft 12, i.e., outside its axis of rotation, and is driven by a magnetic field. The drive element is illustratively made of the same material as used in the embodiment of FIG. 1 for the slide ring 6. The separate external adjusting element is shown here as a simple permanent magnet 18 of which the magnetic field passes through the window 2' and through the non-magnetic wall of the tube 1' already described in relation to the embodiment of FIG. 1.

The drive element 17 can be actuated and the prism 11 can be rotated by moving the magnet 18 near, or by moving it circularly about the endoscope tip shown in FIG. 2.

Because of the reasons cited in the discussion of FIG. 1, difficulties arise when accurately adjusting the two desired angular positions of the prism 11 whereby the desired viewing direction coincides with the directions of the dashed lines 14 or 16. Furthermore, the prism 11 must be secured in the set positions against accelerational displacements.

On that account the embodiment provides a spring-loaded detent device comprising a leaf spring 19, which is affixed at one end by the shown rivet 20 to the wall of the tube 1'. At its free end the leaf spring 19 is sinuous in the form of two detent troughs 21, 21' allowing resilient engagement by the corner of the prism 11 adjacent to the drive element 17. The corner engages the detent trough 21 for the angular position of the prism 11 shown in solid lines. Following magnetic rotation of the prism 11 through an angle 15, the corner snaps into the other detent trough 21', as shown in the Figure. Once there has been a switch in detent engagement, the magnet 18 may be moved away and the new angular position of the prism 11 shall be secured by the detent device until the next adjustment.

The drive elements 6, 17 of both shown embodiments also may assume the shape of elongated structures made of a magnetically permeable material which, on account of their geometric anisotropy, always align themselves along the magnetic field lines of an externally applied magnetic field and which shall be rotated into adjustment by rotating the applied magnetic field. This design is especially applicable to the embodiment of FIG. 2. As regards the embodiment of FIG. 1, the slide ring 6 might be made of non-magnetic material and it might contain a drive element running transversely to the axis of the tube 1, the drive element rotating the ring 6. Such a design might be applicable to rotating a polarizing filter.

The drive elements 6, 17 of the shown embodiments also may be permanent magnets which very forcefully respond to externally applied magnetic fields.

The shown embodiments above contain inner elements 5, 11 in the distal zone of an endoscope stem. Similar designs, however, also may be used in the proximal endoscope main case adjoining the stem zone in order to adjust from that site, for instance, the ocular lens elements or to rotate, for instance, a reflecting prism by means of which the beam can be switched between two viewing directions, for instance in a camera and an ocular. Such magnetic adjustment elements also may be used for other actuations inside the endoscope, illustratively to drive electric switches or to switch valves of gas or liquid lines running through the inner endoscope.

In the above illustrative embodiments, one magnetically displaceable drive element 6, 17 is used in each case at the displaceable components 5, 17. However, several drive elements also may be used that might be actuated also by several magnets externally in attractive or repelling manner.

What is claimed is:

1. An endoscope with a sealed housing wall (1, 1') and an element (5, 11) configured therein, said element being adjustable by means of a drive element (6, 17) affixed thereto and itself powered through said wall by a magnet (7, 18) configured outside said wall, wherein the element (5, 11) is mechanically secured into specific adjusted positions by means of a securing device (8, 9, 10; 21, 21') at a retention force such that the element can be displaced by a force of the magnets (7, 18) from one adjusted position into another adjusted position and wherein the magnet (7, 18) is designed to be mechanically separate from the endoscope (1, 1') and to be brought into magnetical engagement therewith.

2. The endoscope as claimed in claim 1, wherein the securing device is a spring-loaded detent system (9, 19).

3. The endoscope as claimed in claim 1, wherein the adjustable element is a pivoting device (11, 12) mounted in a distal end zone of the endoscope (1') at an objective (4', 5'), said pivoting device being adapted to adjust a viewing direction (14, 16) of the endoscope.

* * * * *

UNITED STATES PATENT AND TRADEMARK OFFICE
CERTIFICATE OF CORRECTION

PATENT NO.    : 6,537,210 B1                                                Page 1 of 1
DATED         : March 25, 2003
INVENTOR(S)   : Wulfsberg It is certified that error appears in the above-identified patent and that said Letters Patent is hereby corrected as shown below:

<u>Title page,</u>
Item [57], ABSTRACT, please delete the entire ABSTRACT and insert -- An endoscope with a hermetic housing wall (1) and containing an optic element (5, 11) that is adjusted by a drive element (6, 17) powered, in turn, by a magnet (7, 18) configured outside the housing wall (1). The optic elements (5, 11) can be held in specific adjustment positions by a detent device (9, 10, 19) such that the force of the magnet (7, 18) shall move the elements from one adjustment position into another. The magnet (7, 18) is mechanically separate from the endoscope. --

Signed and Sealed this

Twenty-second Day of July, 2003

JAMES E. ROGAN
*Director of the United States Patent and Trademark Office*